(12) United States Patent
Igawa et al.

(10) Patent No.: US 9,701,671 B2
(45) Date of Patent: Jul. 11, 2017

(54) ORGANIC COMPOUND, ELECTROCHROMIC ELEMENT CONTAINING THE SAME, OPTICAL FILTER, LENS UNIT, IMAGING DEVICE, AND WINDOW COMPONENT

(71) Applicant: CANON KABUSHIKI KAISHA, Tokyo (JP)

(72) Inventors: Satoshi Igawa, Fujisawa (JP); Kenji Yamada, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/047,508

(22) Filed: Feb. 18, 2016

(65) Prior Publication Data

US 2016/0246152 A1    Aug. 25, 2016

(30) Foreign Application Priority Data

Feb. 20, 2015  (JP) ................. 2015-032002
Jan. 21, 2016  (JP) ................. 2016-009835

(51) Int. Cl.
*G02F 1/15*      (2006.01)
*G02F 1/153*     (2006.01)
(Continued)

(52) U.S. Cl.
CPC ......... *C07D 409/14* (2013.01); *C07D 401/04* (2013.01); *C07F 9/65583* (2013.01);
(Continued)

(58) Field of Classification Search
CPC .......... G02F 1/15; G02F 1/153; G02F 1/1533; G02F 1/163; G02F 2001/151;
(Continued)

(56) References Cited

U.S. PATENT DOCUMENTS 7,056,348 B2 *  6/2006  Sauter .................... A61K 8/492
                                              548/312.1
8,378,092 B2 *  2/2013  Follmann ............. C07D 333/40
                                              540/1
(Continued)

FOREIGN PATENT DOCUMENTS

JP       2007219272 A    8/2007
WO       2011046222 A1   4/2011

*Primary Examiner* — Loha Ben
(74) *Attorney, Agent, or Firm* — Canon U.S.A., Inc., IP Division

(57) ABSTRACT

Provided is an organic compound represented by general formula (1) or (2):

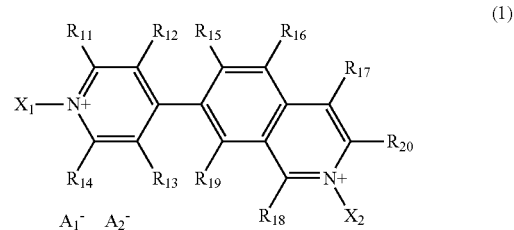

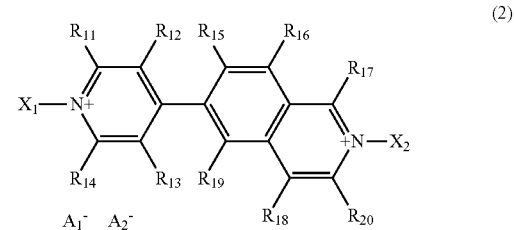

where in general formulae (1) and (2), $X_1$ and $X_2$ are each independently selected from a substituted or unsubsti-
(Continued)

tuted alkyl group and a substituted or unsubstituted aralkyl group, and $R_{11}$ to $R_{20}$ represent a hydrogen atom or a substituent. $A_1^-$ and $A_2^-$ each independently represent a monovalent anion.

17 Claims, 3 Drawing Sheets

(51) Int. Cl.
*C07D 401/04* (2006.01)
*C07D 409/14* (2006.01)
*C07F 9/62* (2006.01)
*G02F 1/163* (2006.01)
*C07F 9/6558* (2006.01)

(52) U.S. Cl.
CPC .......... *G02F 1/1521* (2013.01); *G02F 1/1533* (2013.01); *G02F 1/163* (2013.01); *G02F 1/15* (2013.01); *G02F 2001/151* (2013.01)

(58) Field of Classification Search
CPC ....... H01L 51/00; C09K 11/06; C07F 9/5022; C07F 9/62; C07F 9/65583; C07F 9/65586; C07D 401/04; C07D 409/14; C07D 311/60; C07D 277/22
USPC ............ 359/265, 271, 273, 275; 540/1, 587; 536/18.4
See application file for complete search history.

(56) References Cited

U.S. PATENT DOCUMENTS 8,912,224 B2 * 12/2014 Czechtizky ......... C07F 9/65586
   514/369
9,440,941 B2 * 9/2016 Czechtizky .......... C07D 311/60
2015/0090974 A1 * 4/2015 Kim ....................... C09K 11/06
   257/40

* cited by examiner

ORGANIC COMPOUND, ELECTROCHROMIC ELEMENT CONTAINING THE SAME, OPTICAL FILTER, LENS UNIT, IMAGING DEVICE, AND WINDOW COMPONENT

BACKGROUND OF THE INVENTION

Field of the Invention

The present disclosure relates to an organic compound with electrochromic properties, an electrochromic element containing this organic compound, an optical filter, a lens unit, an imaging device, and a window component.

Description of the Related Art

An electrochromic element is a device that has a pair of electrodes and an electrochromic layer between the electrodes. By applying voltage across the electrodes, it is possible to adjust the amount of light passing through the electrochromic layer.

Those materials that change their optical absorption properties (colors and optical transmittance) through electrochemical redox reaction are called electrochromic (sometimes abbreviated to "EC" hereinafter) materials. There are a wide variety of EC materials that are known, including inorganic, polymeric, and organic low-molecular weight materials.

Using such materials, EC elements have been applied to equipment such as automotive light-control mirrors and electronic paper. The operation of these kinds of equipment is based on the nature of EC materials: various color tones can be displayed according to the choice of materials. Increasing the range of color tones EC materials can produce will open up the possibility for more widespread use of EC elements.

For example, if EC elements are applied to full-color displays or similar, materials that turn cyan, magenta, and yellow will be needed. Further increasing the range of applications will require increasing the range of color tones EC materials can produce. Stability in coloration and breaching and durability in long and repeated use also need to be improved.

Japanese Patent Laid-Open No. 2007-219272 describes a 3,4'-bipyridine derivative that is colored in its reduced state and an electrochromic element that turns yellow.

International Publication No. WO 2011/046222 describes an organic compound that is classified as a pyridine derivative and is colored in its reduced state. An electrochromic element that turns cyan, magenta, and yellow is also described in this publication.

The 3,4'-bipyridine derivative described in Japanese Patent Laid-Open No. 2007-219272 is a compound that displays a yellow color by absorbing light in the blue spectrum, and the electrochromic element in the same publication contains this compound. For the commercialization of electrochromic elements, the compounds described in these publications alone are not sufficient and more need to be studied.

SUMMARY OF THE INVENTION

An aspect of the present disclosure provides an organic compound that changes its transmittance for light in the blue spectrum through redox reaction.

An aspect of the disclosure provides an organic compound represented by general formula (1) or (2):

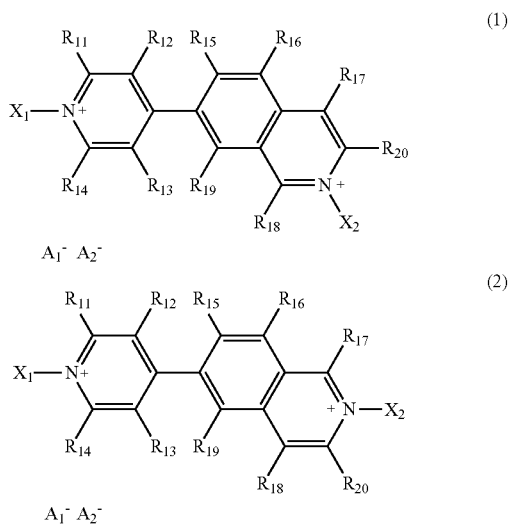

In general formulae (1) and (2), $X_1$ and $X_2$ are each independently selected from an alkyl group and a substituted or unsubstituted aralkyl group. $R_{11}$ to $R_{20}$ represent a hydrogen atom or a substituent. The substituent is any of an alkyl group, an alkoxy group, a substituted or unsubstituted aralkyl group, a substituted or unsubstituted aryl group, a substituted or unsubstituted heterocyclic group, a substituted amino group, a halogen atom, and an acyl group. $A_1^-$ and $A_2^-$ each independently represent a monovalent anion.

Further features of the present disclosure will become apparent from the following description of exemplary embodiments with reference to the attached drawings.

DESCRIPTION OF THE EMBODIMENTS

Figure 1:
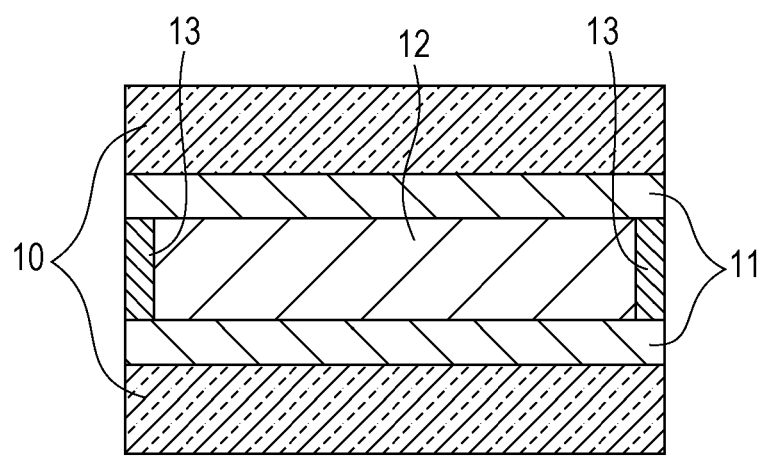
FIG. 1 is a cross-sectional schematic view of an example of an electrochromic element according to an embodiment of the present disclosure.

An aspect of the present disclosure is an organic compound having electrochromic properties. Organic compounds having electrochromic properties are also called electrochromic compounds. In this embodiment, an electrochromic compound may be referred to as an EC compound. Likewise, a material that absorbs light in the blue spectrum may be described as a material that displays a yellow color. In this embodiment, the blue spectrum refers to the range of wavelengths of 440 nm or more and 480 nm or less. In this embodiment, being colored or turning into any color means that the transmittance of the material for a particular wavelength decreases.

The organic compound according to an aspect of the disclosure is an electrochromic compound represented by general formula (1) or (2):

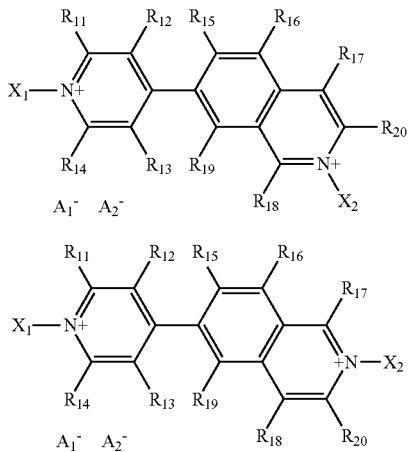

In general formulae (1) and (2), $X_1$ and $X_2$ are each independently selected from an alkyl group and a substituted or unsubstituted aralkyl group. $R_{11}$ to $R_{20}$ represent a hydrogen atom or a substituent. The substituent is any of an alkyl group, an alkoxy group, a substituted or unsubstituted aralkyl group, a substituted or unsubstituted aryl group, a substituted or unsubstituted heterocyclic group, a substituted amino group, a halogen atom, and an acyl group. $A_1^-$ and $A_2^-$ each independently represent a monovalent anion.

The alkyl group which can be represented by $X_1$, $X_2$, and $R_{11}$ to $R_{20}$ may be an alkyl group containing one to eight carbon atoms. Linear, branched, and cyclic alkyl groups can be used.

To be more specific, the alkyl group can be a methyl, ethyl, normal propyl, isopropyl, normal butyl, tertiary butyl, octyl, cyclohexyl, trifluoromethyl, or similar group.

The alkyl group may have a halogen atom, preferably a fluorine atom, or an ester or cyano group as a substituent in place of a hydrogen atom.

The alkyl group may have a terminal absorptive group with which the alkyl group can adsorb onto the surface of a porous electrode. Specific examples of adsorptive groups include carboxyl, sulfonic, phosphonic, phosphoric, and trialkoxysilyl groups.

The substituted or unsubstituted aralkyl group which can be represented by $X_1$, $X_2$, and $R_{11}$ to $R_{20}$ can be a benzyl, phenethyl, or similar group. The aralkyl group may have a substituent. To be more specific, the aralkyl group may have an alkyl group containing one to eight carbon atoms or an alkoxy group containing one to eight carbon atoms.

The alkoxy group which can be represented by $R_{11}$ to $R_{20}$ may be an alkoxy group containing one to eight carbon atoms. Linear, branched, and cyclic alkoxy groups can be used. To be more specific, the alkoxy group can be a methoxy, ethoxy, isopropyloxy, tertiary butyloxy, octyloxy, cyclohexyloxy, trifluoromethyloxy, or similar group. The alkoxy group may have a halogen atom, preferably a fluorine atom, as a substituent in place of a hydrogen atom.

The substituted or unsubstituted aryl group which can be represented by $R_{11}$ to $R_{20}$ can be a phenyl, biphenyl, terphenyl, fluorenyl, naphthyl, fluoranthenyl, anthryl, phenanthryl, pyrenyl, tetracenyl, pentacenyl, triphenylenyl, peryleny, or similar group.

When substituted, the aryl group may have at least one of a halogen atom, an alkyl group containing one to eight carbon atoms, and an alkoxy group containing one to eight carbon atoms.

The substituted or unsubstituted heterocyclic group which can be represented by $R_{11}$ to $R_{20}$ can be a thienyl, pyrrolyl, pyridyl, oxazolyl, oxadiazolyl, thiazolyl, thiadiazolyl, terthienyl, quinolyl, isoquinolyl, carbazolyl, or similar group.

When substituted, the heterocyclic group may have at least one of an alkyl group containing one to eight carbon atoms or an alkoxy group containing one to eight carbon atoms.

The substituted amino group which can be represented by $R_{11}$ to $R_{20}$ is an amino group having a substituent in place of a hydrogen atom. The substituent is an alkyl, aralkyl, or aryl group.

To be more specific, the substituted amino group can be a dimethylamino, diethylamino, dibenzylamine, diphenylamino, ditolylamino, dianisolylamino, or similar group.

The halogen atom which can be represented by $R_{11}$ to $R_{20}$ can be a fluorine, chlorine, bromine, iodine, or similar atom.

The acyl group which can be represented by $R_{11}$ to $R_{20}$ can be an acetyl, benzoyl, or similar group.

$A_1^-$ and $A_2^-$, which may be of the same kind or different, are selected from anions such as $PF_6^-$, $ClO_4^-$, $BF_4^-$, $AsF_6^-$, $SbF_6^-$, $CF_3SO_3^-$, and $(CF_3SO_2)_2N^-$ and halide anions such as $Br^-$, $Cl^-$, and $I^-$. It is preferred that each of $A_1^-$ and $A_2^-$ be $PF_6^-$, $ClO_4^-$, $BF_4^-$, or $(CF_3SO_2)_2N^-$, more preferably both being anions of the same kind.

The organic compound according to an aspect of the disclosure, having a structure represented by general formula (1) or (2), is highly transparent when dissolved in solvent.

The production of the organic compound according to an aspect of the disclosure is not limited to any particular method. Here are some examples of possible production methods. Allowing organic compounds according to general formulae (3) and (4) to react with a halide in a certain solvent, followed by anion-exchange reaction of the product with a salt containing the desired anion in a certain solvent, produces compounds according to general formulae (1) and (2), respectively. By selecting a particular combination of solvent and reaction temperature, it is possible to allow only one of the imine structures in the pyridine and isoquinoline moieties to be involved in the reaction. It is also possible to repeat reactions to introduce different substituents into the pyridine and isoquinoline moieties.

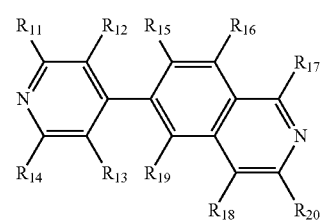

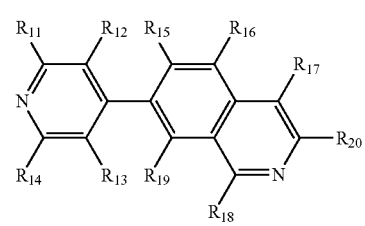

The compounds according to general formulae (3) and (4) can be obtained through a coupling reaction between a boronic or tin derivative of pyridine and a halogenated isoquinoline in an appropriate solvent in the presence of a palladium catalyst and a base.

Here is an example of a route for the synthesis of an organic compound according to an aspect of the disclosure represented by general formula (2). Exchanging the positions of bromine and $R_{15}$ in a starting compound in this route for the synthesis of a compound according to general formula (2) results in producing an organic compound represented by general formula (1) in the same way as in the synthesis of a compound according to general formula (2). Each of $R_{11}$ to $R_{20}$, $X_1$ and $X_2$, and $A_1^-$ and $A_2^-$ in the synthesis route has the same meaning as in general formulae (1) and (2).

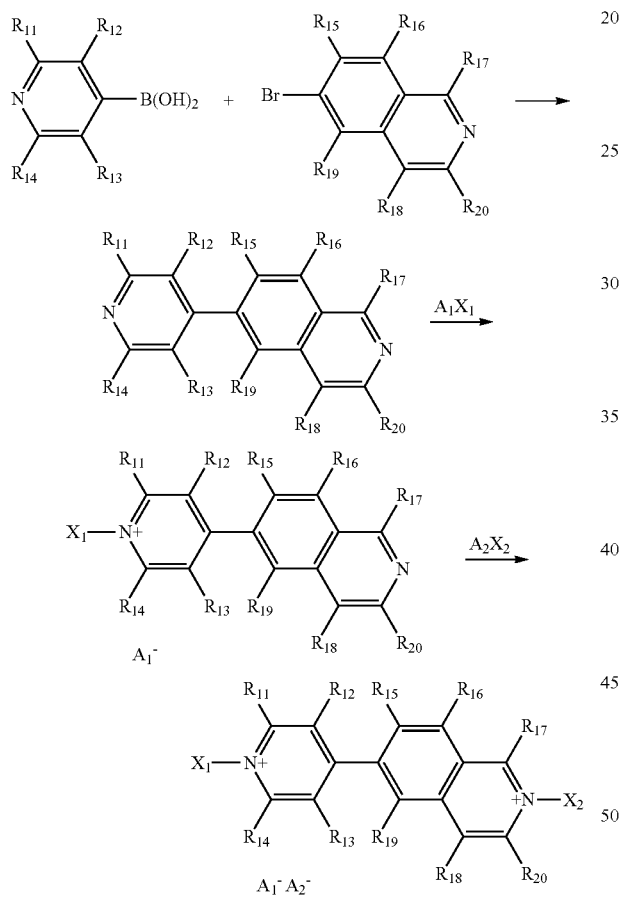

The following are some specific examples of structural formulae for organic compounds according to an aspect of the disclosure. Note that these are not the only compounds according to an aspect of the disclosure.

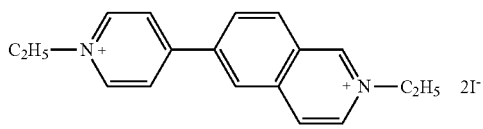

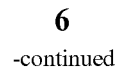

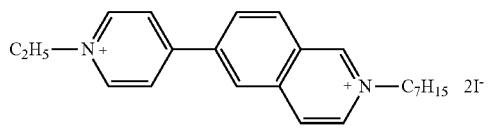

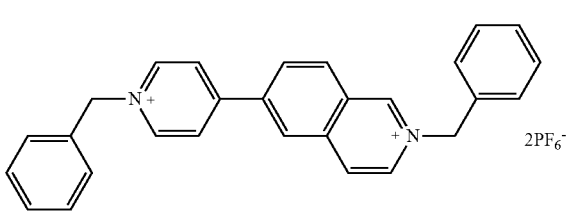

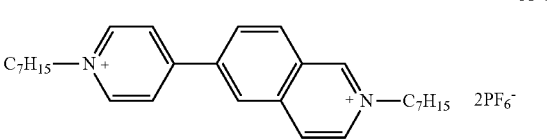

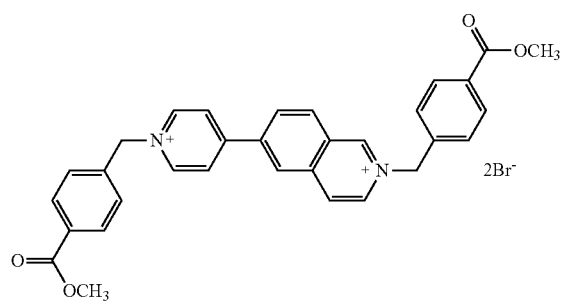

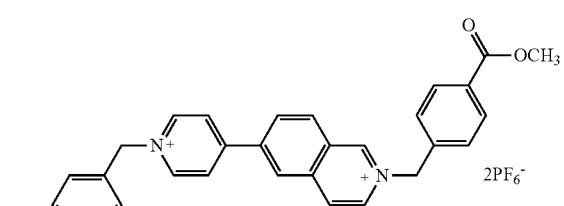

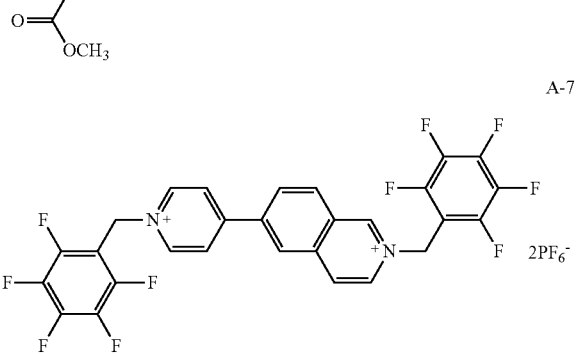

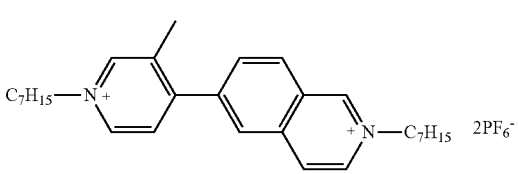

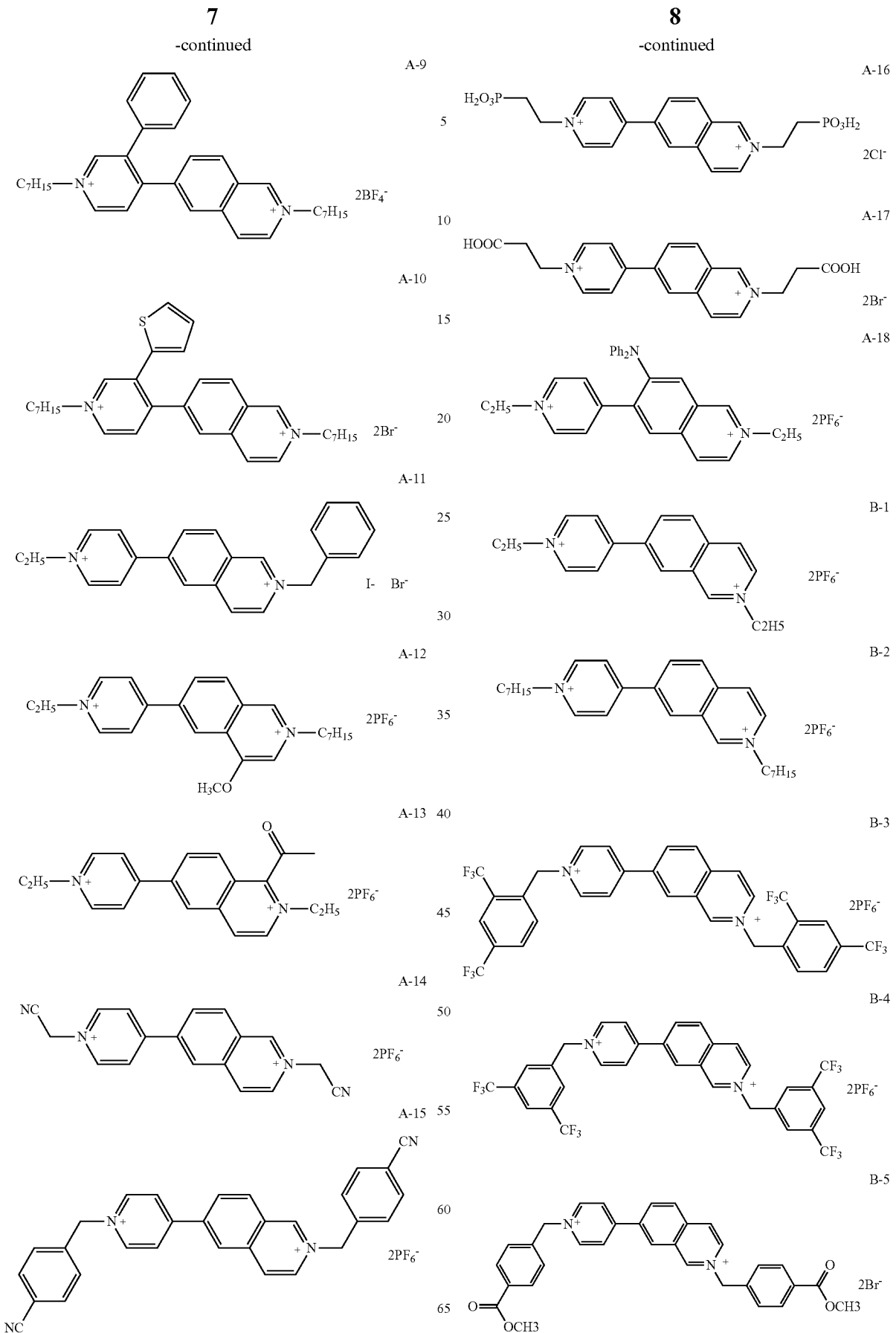

-continued

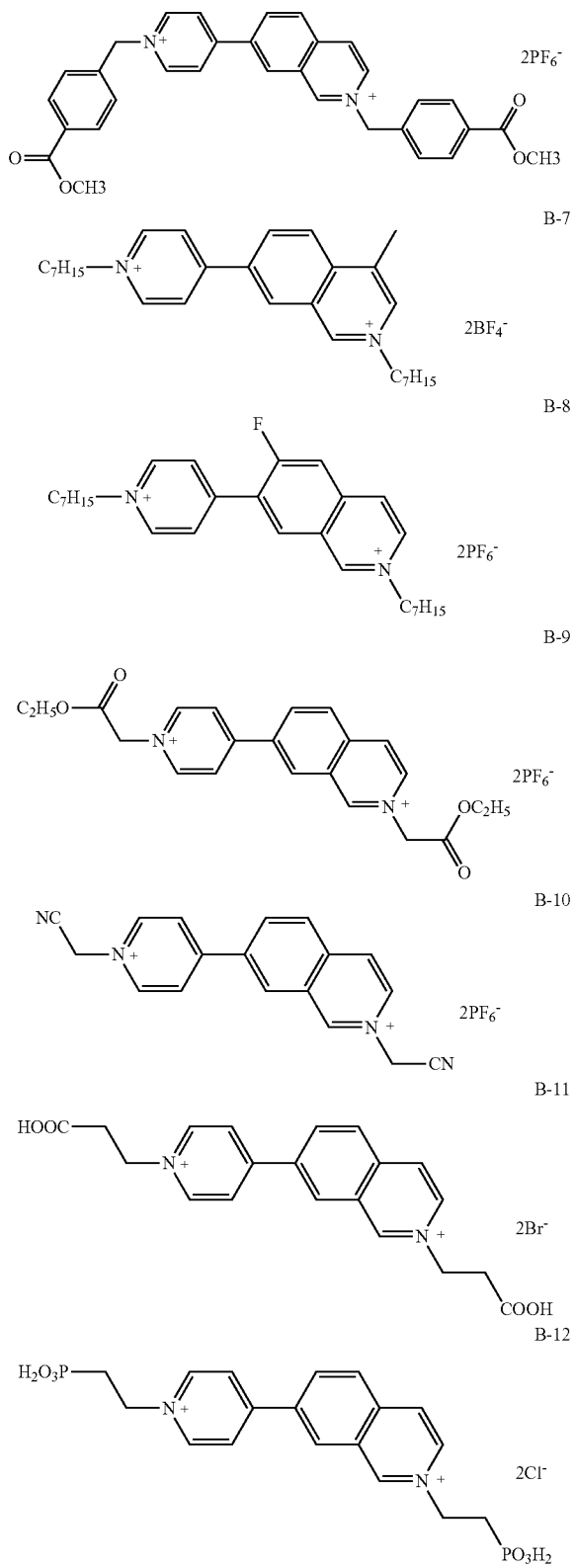

An application of the EC organic compound according to an aspect of the disclosure is an electrochromic layer of an electrochromic element.

The following describes an electrochromic element according to this embodiment with reference to a drawing. In the description that follows, an electrochromic element may be referred to as an EC element.

The EC element illustrated in FIG. 1 has a pair of transparent electrodes 11 and an EC layer 12 between the electrodes. The EC layer 12 contains an electrolyte and an EC organic compound according to an aspect of the disclosure. The distance between the electrodes is constant because of a spacer 13. The electrodes of the EC element are sandwiched between a pair of transparent substrates 10.

The EC layer 12 contains an organic compound according to an aspect of the disclosure. The EC layer may have a layer of the EC compound and a layer of the electrolyte. Alternatively, the EC layer may be a solution containing the EC compound and the electrolyte. It is preferred that the EC layer of the EC element according to this embodiment be a solution.

The following describes the individual structural components of the EC element according to this embodiment.

The electrolyte can be any kind of salt that dissociates into ions and is highly soluble in the solvent used therewith or, for solid electrolytes, highly compatible with the medium used therewith. Electron-donating electrolytes can be used. Electrolytes of this type can also be called supporting electrolytes.

For example, the electrolyte can be an inorganic ionic salt such as an alkali metal salt or an alkaline-earth metal salt, a quaternary ammonium salt, or a cyclic quaternary ammonium salt.

Specific examples include alkali metal salts containing Li, Na, or K, such as $LiClO_4$, $LiSCN$, $LiBF_4$, $LiAsF_6$, $LiCF_3SO_3$, $LiPF_6$, $LiI$, $NaI$, $NaSCN$, $NaClO_4$, $NaBF_4$, $NaAsF_6$, $KSCN$, and $KCl$, quaternary ammonium salts such as $(CH_3)_4NBF_4$, $(C_2H_5)_4NBF_4$, $(n-C_4H_9)_4NBF_4$, $(n-C_4H_9)_4NPF_6$, $(C_2H_5)_4NBr$, $(C_2H_5)_4NClO_4$, $(n-C_4H_9)_4NClO_4$, and cyclic quaternary ammonium salts.

The solvent for the EC organic compound and the electrolyte can be of any kind in which the EC organic compound and the electrolyte are soluble. Polar solvents can be used.

Specific examples include water and organic polar solvents such as methanol, ethanol, propylene carbonate, ethylene carbonate, dimethylsulfoxide, dimethoxyethane, γ-butyrolactone, γ-valerolactone, sulfolane, dimethylformamide, tetrahydrofuran, acetonitrile, propionitrile, benzonitrile, dimethylacetamide, methylpyrrolidinone, and dioxolane.

This EC medium may be mixed with, for example, a polymer or a gelling agent for higher viscosity or gelation.

The polymer can be of any kind. Examples include polyacrylonitrile, carboxymethylcellulose, polyvinyl chloride, polyethylene oxide, polypropylene oxide, polyurethane, polyacrylate, polymethacrylate, polyamide, polyacrylamide, polyester, and Nafion®.

The following describes the transparent substrates and the transparent electrodes. The transparent substrates 10 can be made of, for example, colorless or colored glass, toughened glass, or colorless or colored transparent resin. In this embodiment, being transparent means that the material has a transmittance of 90% or more for visible light.

Specific examples include polyethylene terephthalate, polyethylene naphthalate, polynorbornene, polyamide, polysulfone, polyethersulfone, polyether ether ketone, polyphenylene sulfide, polycarbonate, polyimide, and polymethyl methacrylate.

The electrode materials 11 can be, for example, a metal or metal oxide such as indium tin oxide (ITO), fluorine-doped tin oxide (FTO), tin oxide (NESA), indium zinc oxide (IZO), silver oxide, vanadium oxide, molybdenum oxide, gold, silver, platinum, copper, indium, or chromium, a silicon-based material such as polycrystalline or amorphous silicon, or a carbon material such as carbon black, graphite, or glassy carbon.

Those conductive polymers that have enhanced conductivity as a result of doping or similar can also be used, including polyaniline, polypyrrole, polythiophene, polyacetylene, polyparaphenylene, and the polyethylenedioxythiophene (PEDOT)-polystyrene sulfonate complex.

There may be a porous electrode on the electrodes. The porous electrode may have surface and internal micropores or be in the shape of rods or wires for increased surface area.

The porous electrode can be made of, for example, a metal, a metal oxide, or carbon.

Examples of metal oxides that can be used include titanium oxide, tin oxide, iron oxide, strontium oxide, tungsten oxide, zinc oxide, tantalum oxide, vanadium oxide, indium oxide, nickel oxide, manganese oxide, and cobalt oxide.

The spacer 13, disposed between the electrodes 11, provides a space to enclose the solution 12 containing the EC organic compound according to an aspect of the disclosure and can be made of polyimide, polytetrafluoroethylene, fluororubber, epoxy resin, or similar. The spacer allows the interelectrode distance of the EC element to be maintained.

An EC element according to this embodiment may have a liquid injection port formed by the electrodes and the spacer. Introducing a composition containing the EC organic compound through the liquid injection port, covering the injection port with a sealing member, and tightly securing the sealed portion with an adhesive agent or similar completes the element.

The sealing member also serves to keep the adhesive agent and the EC organic compound out of contact with each other. The sealing member can be in any shape. For example, the sealing member may have a tapered shape, such as a wedge shape.

The production of the EC element according to this embodiment is not limited to any particular method. Any method can be used in which a pre-prepared liquid 12 containing the EC organic compound is injected into the space between a pair of electrode substrates using vacuum impregnation, atmospheric impregnation, the meniscus method, or similar.

An EC element according to this embodiment may contain, in addition to the organic compound according to an aspect of the disclosure, a second organic compound different from the first one. Multiple second organic compounds may also be used. The second organic compound can be a compound that is colored in its oxidized state, a compound that is colored in its reduced state, or a compound that combines these two qualities, preferably a compound that is colored in its oxidized state because the organic compound according to an aspect of the disclosure is colored in its reduced state.

Being colored in its oxidized state means that the compound has a lower transmittance for visible light in its oxidized state than in its reduced state.

The organic compound according to an aspect of the disclosure turns yellow when chemically reduced, and using it in combination with a material in any other color allows the EC element to produce a desired color. The second organic compound in its colored state can have an absorption wavelength in the range of 400 nm or more and 800 nm or less, preferably 420 nm or more and 700 nm or less.

Having an absorption wavelength in a particular range means that the maximum absorption peak in the absorption spectrum of the compound falls within the particular range.

By using the compound according to an aspect of the disclosure in combination with two or more other compounds, it is possible to produce an EC element that absorbs light in the entire visible spectrum and turns black.

Examples of second organic compounds according to this embodiment include the following.

Examples of EC compounds that are colored in their oxidized state include phenazine compounds such as 5,10-dihydro-5,10-dimethylphenazine and 5,10-dihydro-5,10-diethylphenazine, metallocene compounds such as ferrocene, tetra-t-butylferrocene, and titanocene, phenylenediamine compounds such as N,N',N,N'-tetramethyl-p-phenylenediamine, and pyrazoline compounds such as 1-phenyl-2-pyrazoline.

Examples of compounds that are colored in their reduced state other than the compound according to an aspect of the disclosure include viologen compounds such as N,N'-diheptyl bipyridinium diperchlorate, N,N'-diheptyl bipyridinium ditetrafluoroborate, N,N'-diheptyl bipyridinium dihexafluorophosphate, N,N'-diethyl bipyridinium diperchlorate, N,N'-diethyl bipyridinium ditetrafluoroborate, N,N'-diethyl bipyridinium dihexafluorophosphate, N,N'-dibenzyl bipyridinium diperchlorate, N,N'-dibenzyl bipyridinium ditetrafluoroborate, N,N'-dibenzyl bipyridinium dihexafluorophosphate, N,N'-diphenyl bipyridinium diperchlorate, N,N'-diphenyl bipyridinium ditetrafluoroborate, and N,N'-diphenyl bipyridinium dihexafluorophosphate, anthraquinone compounds such as 2-ethylanthraquinone, 2-t-butylanthraquinone, and octamethylanthraquinone, ferrocenium salt compounds such as ferrocenium tetrafluoroborate and ferrocenium hexafluorophosphate, and styryl compounds.

Of these, phenazine, ferrocene, metallocene, phenylenediamine, and pyrazoline compounds are preferred for use as second organic compounds.

When a given compound is contained in the EC layer of the EC element according to this embodiment, its presence in the EC element can be detected through known processes of extraction and analysis, such as chromatographic extraction and NMR analysis. If the electrochromic layer is solid, it is possible to use TOF-SIMS or similar for analysis.

The applications of the EC element according to this embodiment include optical filters, lens units, imaging devices, and window components. An optical filter according to an aspect of the disclosure includes an EC element and an active element connected to the EC element. The active element is configured to drive the electrochromic element and control the amount of light that passes through the electrochromic element. The active element can be, for example, a transistor or an MIM element. The transistor may contain an oxide semiconductor such as InGaZnO in its active region.

A lens unit according to an aspect of the disclosure includes an optical filter according to an aspect of the disclosure and an imaging optical system. The imaging optical system is a lens group including multiple lenses. The lens unit may have the optical filter somewhere between a lens and another lens or, if attached to an imaging device, on the image pick-up element side or the other side with respect to the lenses.

An imaging device according to an aspect of the disclosure has an optical filter and an image pick-up element configured to receive light transmitted through the optical filter. The imaging device according to an aspect of the disclosure can be, for example, a digital camera or digital video camera. An imaging device according to an aspect of the disclosure may have the optical filter disposed immediately before the image pick-up element. Being disposed immediately before the image pick-up element means that there is no other component between the image pick-up element and the optical filter. If the imaging device has a lens, the optical filter may be disposed on the other side of the lens. Being disposed on the other side of a lens means that the optical filter is in such a position that the lens is between the optical filter and the image pick-up element. If the imaging device has multiple lenses, the optical filter may be disposed somewhere between a lens and another lens.

A window component according to an aspect of the disclosure includes a pair of transparent substrates, an EC element between the transparent substrates, and an active element coupled to the EC element. The amount of light that passes through the transparent substrates can be regulated using the EC element. Adding other components such as a window frame to this window component completes a window. The applications of the window component include, for example, automotive windows, airplane windows, and windows as a building material.

Figure 2:
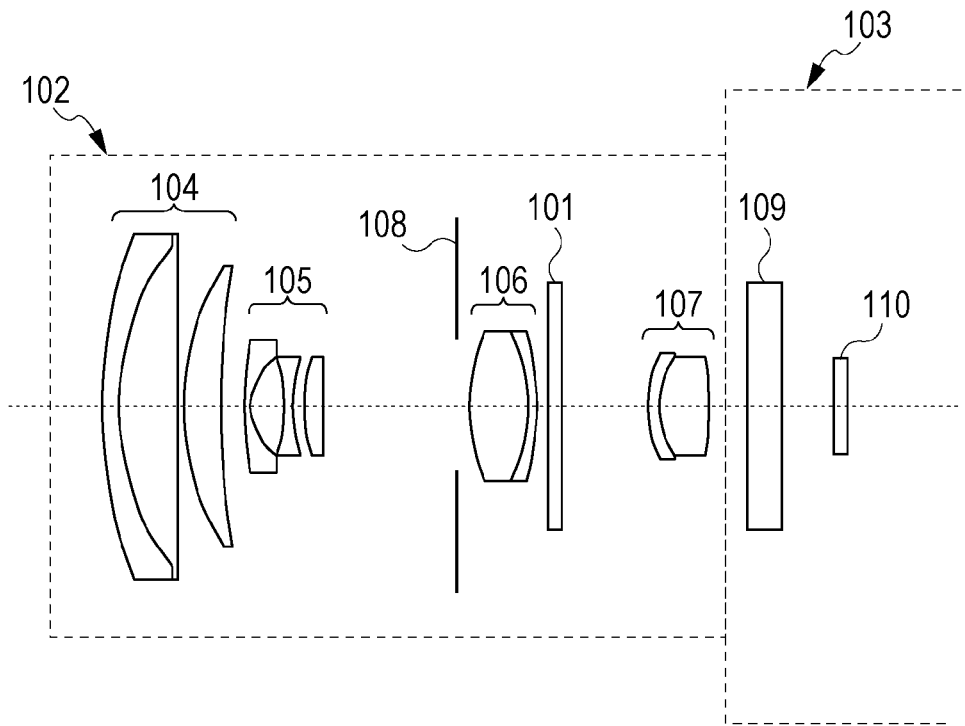
FIG. 2 is a cross-sectional schematic view of an imaging device according to an embodiment of the present disclosure including a lens unit.

FIG. 2 is a schematic view of an imaging device according to this embodiment.

The imaging device according to this embodiment has a lens unit 102 and an image pick-up unit 103. The lens unit 102 is detachably connected to the image pick-up unit 103 via a mount (not illustrated).

The lens unit 102, including multiple lenses or lens groups, serves as a rear-focusing zoom lens, a lens system in which the lenses for focusing are disposed on the image pick-up element side with respect to the diaphragm.

The lens unit 102 has four lens groups (i.e., a first lens group 104 with a positive refractive power, a second lens group 105 with a negative refractive power, a third lens group 106 with a positive refractive power, and a fourth lens group 107 with a positive refractive power), an aperture stop 108 between the second lens group 105 and the third lens group 106, and an optical filter 101 between the third lens group 106 and the fourth lens group 107. Changing the distance between the second lens group 105 and the third lens group 106 for scaling displaces part of the fourth lens group 107, bringing the subject into focus. The individual components are arranged in such a manner that light transmitted through the first to fourth lens groups, the aperture stop 108, and the optical filter 101 is received by an image pick-up element. The amount of light the image pick-up element receives can be regulated using the aperture stop 108 and the optical filter 101. The image pick-up unit 103 has a glass block 109 and an image pick-up element 110.

The glass block 109 is a low-pass filter, a phase plate, a color filter, or similar.

The image pick-up element 110, a sensing section configured to receive light transmitted through the lens unit 102, can be a CCD, a CMOS, or similar. The image pick-up element 110 can also be a photosensor such as a photodiode. Any device configured to acquire and output information on the intensity or wavelength of light can be optionally used.

The imaging device according to this embodiment has the optical filter 101 between the third and fourth lens groups in the optical lens unit. This arrangement is for illustrative purposes and the position of the optical filter 101 in an imaging device according to an aspect of the disclosure is not limited to this. The position of the optical filter 101 can be before or after the aperture stop 108. Likewise, the optical filter 101 can be disposed before any of the first to fourth lens groups, after any of these lens groups, and between any two lens groups.

The optical filter can be smaller in area when placed at the point of convergence. The imaging device according to an aspect of the disclosure also supports many options for the mode of operation of the lens unit. Besides rear-focusing ones, inner-focusing (the lenses for focusing are disposed in front of the diaphragm) and other lens units can be used. Furthermore, the zoom lens can optionally be replaced with a special lens, such as a fisheye or macro lens.

The imaging device according to this embodiment has the optical filter 101 inside the lens unit 102. This arrangement, too, is for illustrative purposes. An imaging device according to an aspect of the disclosure may have a structure in which the EC element as a structural component of the optical filter is inside the lens unit whereas the driver for the EC element is outside the lens unit, i.e., belongs to the image pick-up unit. The driver may include the active element. In such a case, the EC element in the lens unit is wired to the driver for it so that its operation can be controlled.

Moreover, an imaging device according to an aspect of the disclosure may have the optical filter 101 inside the image pick-up unit 103.

Figure 3:
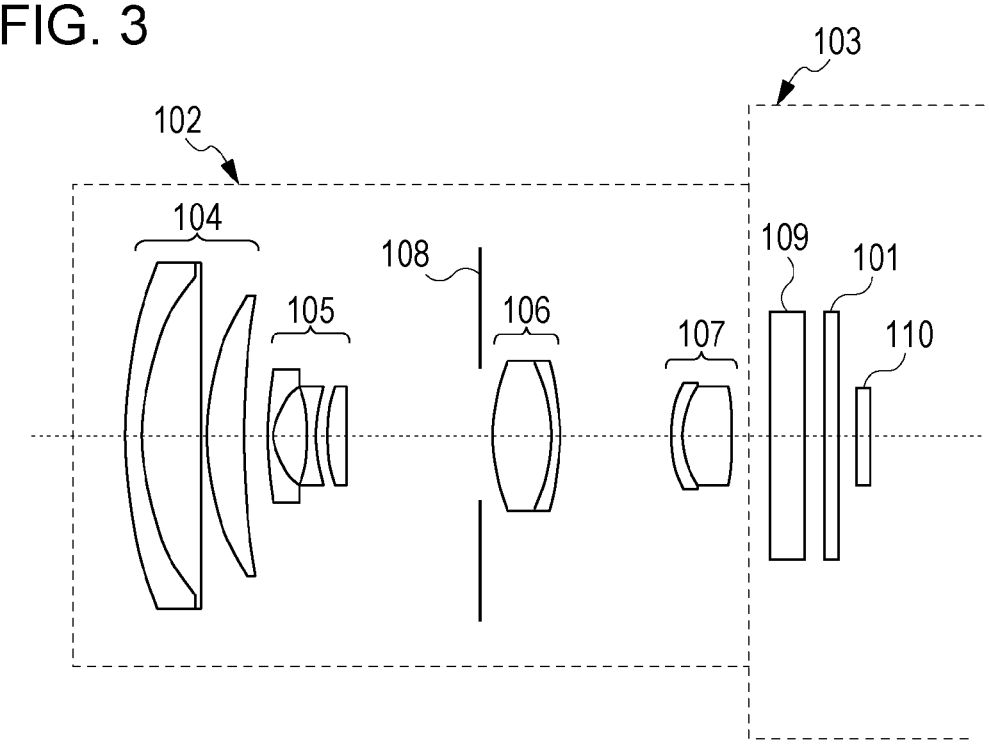
FIG. 3 is a cross-sectional schematic view of an imaging device according to an embodiment of the present disclosure.

FIG. 3 is a schematic view of an imaging device having a structure in which the optical filter 101 is inside the image pick-up unit 103.

The optical filter 101 is disposed between the glass block 109 and the image pick-up element 110, internal components of the image pick-up unit 103. This structure, in which the image pick-up unit 103 contains the optical filter 101, eliminates the need for the lens unit 102 to have an optical filter, allowing for the use of an existing lens unit.

In FIG. 3, the optical filter 101 is disposed between the image pick-up element 110 and the glass block 109. FIG. 3 is for illustrative purposes and the position of the optical filter 101 need not be between the image pick-up element 110 and the glass block 109 as long as the image pick-up element 110 receives light transmitted through the optical filter 101.

Examples of such imaging devices include products having a combination of the control of the amount of light and an image pick-up element, such as cameras, digital cameras, video cameras, digital video cameras, and camera units of cellphones, smartphones, PCs, and tablets.

The lens unit 102 in this embodiment is a rear-focusing zoom lens, a lens system in which the lenses for focusing are disposed behind the diaphragm.

EXAMPLES

The following describes certain aspects of the disclosure in more detail by providing examples. No aspect of the disclosure is limited to these examples.

Example 1

Synthesis of Exemplified Compound A-5

The following materials were charged into a 300-ml flask: 5.6 g (24.6 mmol) of 6-bromoisoquinoline, 3.7 g (29.5 mmol) of 4-pyridineboronic acid, 0.6 g of Pd(PPh$_3$)$_4$, 7.9 g of calcium carbonate, 50 ml of dimethoxyethane, and 50 ml of water. The mixture was stirred at 100° C. under nitrogen atmosphere for 18 hours. After the completion of reaction, the solution was concentrated and extracted by ethyl acetate. The organic layer was washed with water and dried over magnesium sulfate, and the solvent was removed under reduced pressure. The residue was purified by silica gel column chromatography (with ethyl acetate/ethanol (20:1) as eluent), and the collected substance was dispersed and washed in diethyl ether. In this way, 3.0 g of 6-pyridylisoquinoline was obtained (60% yield).

The structure of this compound was confirmed using NMR analysis.

$^1$H NMR (CDCl$_3$, 500 MHz) σ (ppm): 9.33 (s, 1H), 8.76 (m, 2H), 8.61 (d, 1H), 8.11 (d, 1H), 8.09 (s, 1H), 7.88 (dd, 1H), 7.75 (d, 1H), 7.64 (m, 2H)

Then the following materials were charged into a flask: 412 mg (2 mmol) of 6-pyridylisoquinoline, 1.0 g (4.4 mmol) of methyl 4-(bromomethyl)benzoate, and 20 ml of N,N-dimethylformamide. The mixture was stirred at 100° C. for 8 hours. After the completion of reaction, the resulting crystals were collected through filtration and washed with acetonitrile. In this way, 1.1 g of exemplified compound A-5 was obtained (83% yield).

The structure of this compound was confirmed using NMR analysis.

$^1$H NMR (D$_2$O, 500 MHz) σ (ppm): 9.87 (s, 1H), 9.01 (d, 2H), 8.69 (s, 1H), 8.59 (d, 1H), 8.55 (d, 1H), 8.49 (d, 1H), 8.47 (d, 2H), 8.35 (d, 1H) 8.03 (t, 4H), 7.53 (dd, 4H), 5.98 (s, 2H), 5.87 (s, 2H), 3.86 (s, 3H), 3.85 (s, 3H)

Example 2

Synthesis of Exemplified Compound A-6

To an aqueous solution of 0.5 g (0.76 mmol) of exemplified compound A-5, an aqueous solution of 1.0 g of potassium hexafluorophosphate was added dropwise. The mixed solution was stirred for 3 hours at room temperature. The resulting crystals were collected through filtration and washed with isopropyl alcohol and then diethyl ether. In this way, 1.3 g of exemplified compound A-6 was obtained (98% yield).

The structure of this compound was confirmed using NMR analysis.

$^1$H NMR (CD$_3$CN, 500 MHz) σ (ppm): 9.73 (s, 1H), 8.92 (m, 2H), 8.72 (m, 1H), 8.62 (d, 1H), 8.53 (m, 2H), 8.44 (m, 2H), 8.38 (dd, 1H), 8.01 (m, 4H), 7.61 (dd, 4H), 5.96 (s, 2H), 5.87 (s, 2H), 3.90 (s, 3H), 3.89 (s, 3H)

Example 3

Production of Electrochromic Element and Evaluation of Characteristics

Tetrabutylammonium perchlorate as electrolyte was dissolved in propylene carbonate to a concentration of 0.1 M. Organic compound A-6 prepared in Example 2 was then dissolved to a concentration of 40.0 mM. In this way, an EC medium was obtained.

An insulating layer (SiO$_2$) was then formed on a pair of glass substrates having a transparent conductive coating (ITO), covering the four edge portions. A piece of PET film (Teijin DuPont Films Melinex® S, 125 μm thick) was placed between the glass substrates having a transparent electrode coating to specify the distance between the substrates. The substrates and the PET film were then bonded and sealed using an epoxy adhesive agent, except at a point through which the EC medium would be injected. In this way, an empty cell having an injection port was produced.

The EC medium was then injected through the injection port using vacuum impregnation, and the injection port was secured with an epoxy adhesive agent to complete an EC element.

The EC element was highly transparent immediately after production, with its transmittance being approximately 80% across the entire spectrum of visible light.

Figure 4:
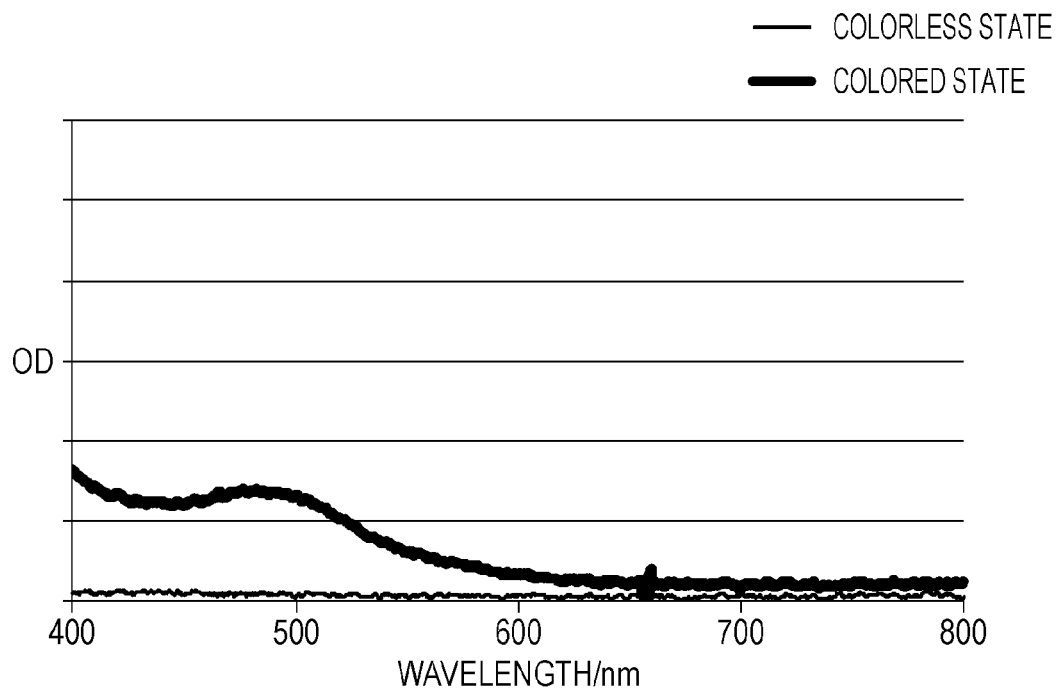
FIG. 4 illustrates an ultraviolet-visible absorption spectrum of exemplified compound A-6 in its colored and colorless states.
Figure 5:
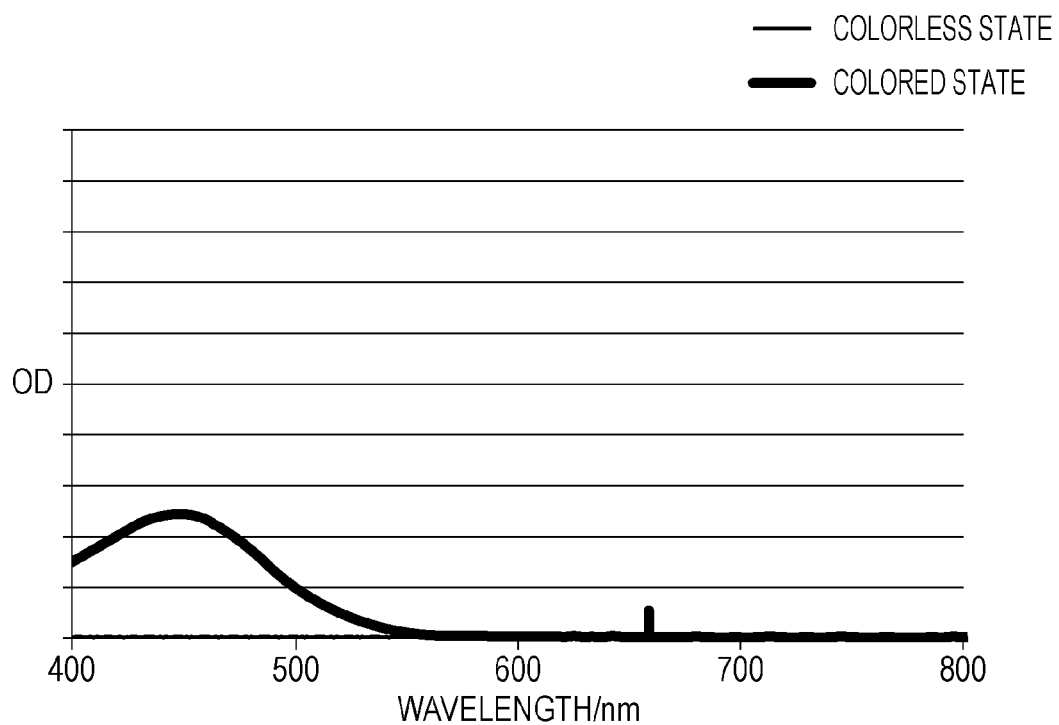
FIG. 5 illustrates an ultraviolet-visible absorption spectrum of exemplified compound B-6 in its colored and colorless states.

Applying a voltage of 3.0 V to the element colored it yellow as a result of absorption by the reduced species of exemplified compound A-6 (λmax=474 nm). Applying −0.5 V breached the element. This element can be reversibly colored and breached. FIG. 4 is an ultraviolet-visible absorption spectrum of the element produced in Example 3. The light source was Ocean Optics DH-2000S Deuterium Halogen Light Source. In FIGS. 4 and 5, the peak at around 650 nm is associated with the measuring instrument and does not represent absorption by the compound.

Example 4

Synthesis of Exemplified Compound B-5

The following materials were charged into a 300-ml flask: 4.0 g (19.2 mmol) of 7-bromoisoquinoline, 2.8 g (23.1 mmol) of 4-pyridineboronic acid, 0.58 g of Pd(PPh$_3$)$_4$, 6.1 g of calcium carbonate, 40 ml of dimethoxyethane, and 40 ml of water. The mixture was stirred at 100° C. under nitrogen atmosphere for 18 hours. After the completion of reaction, the solution was concentrated and extracted by ethyl acetate. The organic layer was washed with water and dried over magnesium sulfate, and the solvent was removed under reduced pressure. The residue was purified by silica gel column chromatography (with ethyl acetate/ethanol (20:1) as eluent), and the collected substance was dispersed and washed in diethyl ether. In this way, 3.3 g of 7-pyridylisoquinoline was obtained (65% yield). The structure of this compound was confirmed using NMR analysis.

$^1$H NMR (CDCl$_3$, 500 MHz) σ (ppm): 9.53 (s, 1H), 8.74 (m, 2H), 8.58 (m, 1H), 8.21 (s, 1H), 7.94 (m, 2H), 7.70 (d, 1H), 7.62 (m, 2H)

Then the following materials were charged into a flask: 412 mg (2 mmol) of 7-pyridylisoquinoline, 1.0 g (4.4 mmol) of methyl 4-(bromomethyl)benzoate, and 20 ml of N,N-dimethylformamide. The mixture was stirred at 100° C. for 8 hours. After the completion of reaction, the resulting crystals were collected through filtration and washed with acetonitrile. In this way, 1.2 g of exemplified compound B-5 was obtained (90% yield). The structure of this compound was confirmed using NMR analysis.

$^1$H NMR (D$_2$O, 500 MHz) σ (ppm): 9.93 (s, 1H), 9.00 (d, 2H), 8.89 (s, 1H), 8.62 (d, 1H), 8.57 (m, 1H), 8.47 (d, 3H), 8.41 (d, 1H), 8.05 (t, 4H), 7.55 (dd, 4H), 6.03 (s, 2H), 5.91 (s, 2H), 3.89 (s, 3H), 3.88 (s, 3H)

Example 5

Synthesis of Exemplified Compound B-6

To an aqueous solution of 0.5 g (0.76 mmol) of exemplified compound B-5, an aqueous solution of 1.0 g of potassium hexafluorophosphate was added dropwise. The mixed solution was stirred for 3 hours at room temperature. The resulting crystals were collected through filtration and washed with isopropyl alcohol and then diethyl ether. In this way, 1.3 g of exemplified compound B-6 was obtained (98% yield). The structure of this compound was confirmed using NMR analysis.

¹H NMR (CD$_3$CN, 500 MHz) σ (ppm): 9.71 (s, 1H), 8.89 (m, 3H), 8.60-8.45 (m, 4H), 8.42 (d, 2H), 8.11 (m, 4H), 7.60 (m, 4H), 5.98 (s, 2H), 5.87 (s, 2H), 3.90 (s, 3H), 3.89 (s, 3H)

Example 6

Production of Electrochromic Element and Evaluation of Characteristics

An element was produced in the same way as in Example 3 except that exemplified compound A-6 was replaced with exemplified compound B-6. Applying a voltage of 3.0 V to the element according to this example colored the element yellow as a result of absorption by the reduced species of exemplified compound B-6 (λmax=447 nm). Applying −0.5 V breached the element, demonstrating reversible coloration and breaching. This element can be reversibly colored and breached. FIG. 5 is an ultraviolet-visible absorption spectrum of the element produced in Example 6.

Example 7

Synthesis of Exemplified Compound A-14

The following materials were charged into a flask: 412 mg (2 mmol) of 6-pyridylisoquinoline, 528 mg (4.4 mmol) of bromoacetonitrile, and 20 ml of acetonitrile. The mixture was stirred for 8 hours with heating under reflux. The reaction solution after the completion of reaction was allowed to cool to room temperature, and ethyl acetate was added. The resulting crystals were collected through filtration and washed with ethyl acetate. In this way, a powder in orange was obtained.

This orange powder was dissolved in water. The solution was stirred at room temperature for 3 hours while an aqueous solution of 1.0 g of potassium hexafluorophosphate was added dropwise. The resulting crystals were collected through filtration and washed with isopropyl alcohol and then with diethyl ether. In this way, 945 mg of exemplified compound A-14 was obtained (82% yield). The structure of this compound was confirmed using NMR analysis.

¹H NMR (CD$_3$CN, 500 MHz) σ (ppm): 9.82 (s, 1H), 9.01 (m, 2H), 8.83 (s, 1H), 8.75 (d, 1H), 8.69 (d, 1H), 8.65 (m, 1H), 8.57 (m, 2H), 8.47 (m, 1H), 5.82 (s, 2H), 5.71 (s, 2H)

Example 8

Production of Electrochromic Element and Evaluation of Characteristics

An element was produced in the same way as in Example 3 except that exemplified compound A-6 was replaced with exemplified compound A-14. Applying a voltage of 2.0 V to the element according to this example colored the element yellow as a result of absorption by the reduced species of exemplified compound A-14 (λmax=470 nm). Applying −0.5 V breached the element, demonstrating reversible coloration and breaching. This element can be reversibly colored and breached.

Example 9

Synthesis of Exemplified Compound B-2

The following materials were charged into a flask: 412 mg (2 mmol) of 7-pyridylisoquinoline, 995 mg (4.4 mmol) of 1-iodoheptane, and 20 ml of acetonitrile. The mixture was stirred for 8 hours with heating under reflux. The reaction solution after the completion of reaction was allowed to cool to room temperature, and ethyl acetate was added. The resulting crystals were collected through filtration and washed with ethyl acetate. In this way, a powder in orange was obtained.

This orange powder was dissolved in water at 50° C. The solution was stirred at room temperature for 3 hours while an aqueous solution of 1.0 g of potassium hexafluorophosphate was added dropwise. The resulting crystals were collected through filtration and washed with isopropyl alcohol and then with diethyl ether. In this way, 1.06 g of exemplified compound B-2 was obtained (76% yield). The structure of this compound was confirmed using NMR analysis.

¹H NMR (CD$_3$CN, 500 MHz) σ (ppm): 9.65 (s, 1H), 8.87 (s, 1H), 8.83 (m, 2H), 8.60-8.45 (m, 4H), 8.41 (d, 2H), 4.71 (t, 2H), 4.59 (t, 2H), 2.13-1.98 (m, 4H), 1.47-1.26 (m, 16H), 0.94-0.85 (m, 6H)

Example 10

Synthesis of Exemplified Compound A-4

The following materials were charged into a flask: 412 mg (2 mmol) of 6-pyridylisoquinoline, 995 mg (4.4 mmol) of 1-iodoheptane, and 20 ml of acetonitrile. The mixture was stirred for 8 hours with heating under reflux. The reaction solution after the completion of reaction was allowed to cool to room temperature, and ethyl acetate was added. The resulting crystals were collected through filtration and washed with ethyl acetate. In this way, a powder in orange was obtained.

This orange powder was dissolved in water at 50° C. The solution was stirred at room temperature for 3 hours while an aqueous solution of 1.0 g of potassium hexafluorophosphate was added dropwise. The resulting crystals were collected through filtration and washed with isopropyl alcohol and then with diethyl ether. In this way, 1.10 g of exemplified compound A-4 was obtained (79% yield). The structure of this compound was confirmed using NMR analysis.

¹H NMR (CD$_3$CN, 500 MHz) σ (ppm): 9.64 (s, 1H), 8.85 (d, 2H), 8.73 (s, 1H), 8.64 (d, 1H), 8.53 (m, 2H), 8.43 (m, 2H), 8.38 (m, 1H), 4.69 (t, 2H), 4.59 (t, 2H), 2.14-1.99 (m, 4H), 1.47-1.26 (m, 16H), 0.95-0.85 (m, 6H)

Example 11

Production of Electrochromic Element and Evaluation of Characteristics

An element was produced in the same way as in Example 3 except that exemplified compound A-6 was replaced with exemplified compound A-4. Applying a voltage of 3.0 V to the element according to this example colored the element yellow as a result of absorption by the reduced species of exemplified compound A-4 (λmax=473 nm). Applying −0.5 V breached the element, demonstrating reversible coloration and breaching. This element can be reversibly colored and breached.

Example 12

Stability in Terms of Durability Against Redox Cycles

The measurement of durability was performed using a glassy carbon working electrode, a platinum counter electrode, and a silver reference electrode. Each compound was dissolved ($5.0 \times 10^{-4}$ mol/L) in a propylene carbonate solution (0.1 mol/L) with tetrabutylammonium hexafluorophosphate as a supporting electrolyte. This solution was repeatedly exposed 10,000 times to a rectangular wave potential program consisting of 3 seconds of constant-potential oxidation at $-1.5$ V (vs. Ag/Ag$^+$), a potential lower than the reduction potential of the compound, and 3 seconds of constant-potential oxidation at 0 V (vs. Ag/Ag$^+$). Table summarizes the change in CV reduction peak current after the 10,000 redox cycles from that before the redox cycles. The percent changes in reduction peak current are representations of the initial current as 100% plus the change from it.

TABLE

| Compound | Change (%) in CV reduction peak current after the 10,000 redox cycles from that before the redox cycles |
|---|---|
| Exemplified compound A-6 | 99% |
| Exemplified compound B-5 | 98% |
| Exemplified compound A-4 | 100% |

As can be seen from the table, the organic compounds according to an aspect of the disclosure experienced little or no change in reduction peak current during 10,000 redox cycles, demonstrating their excellent stability in terms of durability against redox cycles.

As is clear from the foregoing, an aspect of the disclosure, in which a compound represented by general formula (1) is applied to an organic EC element, provides an electrochromic element that absorbs light in the blue spectrum and can be reversibly colored and breached in a stable manner.

As is clear from the foregoing, an aspect of the disclosure, in which a compound represented by general formula (1) is applied to an organic EC element, provides an electrochromic element that absorbs light in the blue spectrum and can be reversibly colored and breached in a stable manner.

The organic compound according to an aspect of the disclosure is an electrochromic material that absorbs light in the blue spectrum and can be reversibly colored and breached in a stable manner through chemical reduction. The applications of this organic compound include EC elements and optical filters, lens units, imaging devices, and other equipment that use an EC element.

An aspect of the present disclosure provides an organic compound that changes its transmittance for light in the blue spectrum through redox reaction.

While the present disclosure has been described with reference to exemplary embodiments, it is to be understood that the disclosure is not limited to the exemplary embodiments provided herein. The scope of the following claims is to be accorded the broadest interpretation so as to encompass all such modifications and equivalent structures and functions.

This application claims the benefit of Japanese Patent Application No. 2015-032002 filed Feb. 20, 2015 and No. 2016-009835 filed Jan. 21, 2016, which are hereby incorporated by reference herein in their entirety.

What is claimed is:

1. An organic compound represented by general formula (1) or (2):

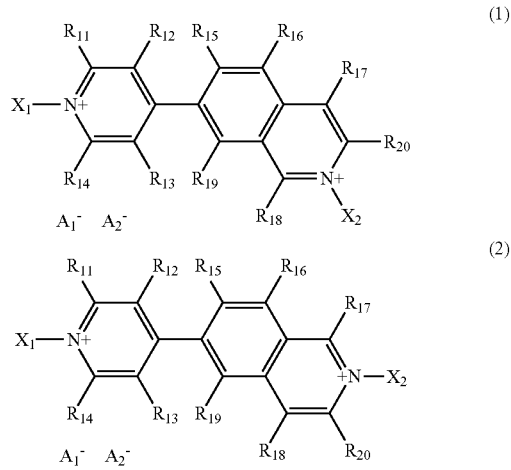

where $X_1$ and $X_2$ are each independently selected from a substituted or unsubstituted alkyl group and a substituted or unsubstituted aralkyl group, and $R_{11}$ to $R_{20}$ are each independently selected from a hydrogen atom and a substituent, the substituent being any of a substituted or unsubstituted alkyl group, a substituted or unsubstituted alkoxy group, a substituted or unsubstituted aralkyl group, a substituted or unsubstituted aryl group, a substituted or unsubstituted heterocyclic group, a substituted amino group, a halogen atom, and an acyl group, and $A_1^-$ and $A_2^-$ each independently represent a monovalent anion.

2. The organic compound according to claim 1, wherein the $X_1$ and the $X_2$ are substituents of the same kind.

3. The organic compound according to claim 2, wherein the $X_1$ and the $X_2$ are the aralkyl groups.

4. The organic compound according to claim 1, wherein all of the $R_{11}$ to the $R_{20}$ are hydrogen atoms.

5. The organic compound according to claim 1, wherein the $A_1^-$ and the $A_2^-$ are anions of the same kind.

6. An electrochromic element comprising a pair of electrodes and an electrochromic layer between the electrodes, the electrochromic layer containing a first organic compound, the first organic compound being an organic compound according to claim 1.

7. The electrochromic element according to claim 6, wherein the electrochromic layer contains a second organic compound different from the first organic compound.

8. The electrochromic element according to claim 7, wherein the second organic compound is any of a phenazine compound, ferrocene, a metallocene compound, a phenylenediamine compound, and a pyrazoline compound.

9. The electrochromic element according to claim 7, wherein the electrochromic element absorbs light with wavelengths of 420 nm or more and 700 nm or less.

10. The electrochromic element according to claim 6, wherein the electrochromic layer is a liquid containing an electrolyte and the first organic compound.

11. An optical filter comprising an electrochromic element according to claim 6 and an active element coupled to the electrochromic element.

12. The optical filter according to claim 11, wherein the active element is configured to drive the electrochromic element and regulate an amount of light passing through the electrochromic element.

13. A lens unit comprising: an optical filter according to claim 11, and an imaging optical system including a plurality of lenses.

14. An imaging device comprising: an imaging optical system including a plurality of lenses, an optical filter according to claim 11, and an image pick-up element configured to receive light transmitted through the optical filter.

15. An imaging device configured to allow an imaging optical system including a plurality of lenses to be attached thereto, the imaging device comprising:
   an optical filter according to claim 11, and an image pick-up element configured to receive light transmitted through the optical filter.

16. A window component comprising:
   a pair of transparent substrates, an electrochromic element according to claim 6 between the transparent substrates, and an active element coupled to the electrochromic element, the window component configured to regulate an amount of light passing through the transparent substrates using the electrochromic element.

17. The window component according to claim 16, wherein the active element is configured to drive the electrochromic element and regulate an amount of light passing through the electrochromic element.

* * * * *